United States Patent [19]

Davern et al.

[11] Patent Number: 5,756,796
[45] Date of Patent: May 26, 1998

[54] METHOD FOR PREPARATION OF ALKENYLSILANES

[75] Inventors: Sean Patrick Davern, Auburn; Binh Thanh Nguyen, Midland, both of Mich.

[73] Assignee: Dow Corning Corporation, Midland, Mich.

[21] Appl. No.: 861,311

[22] Filed: May 19, 1997

[51] Int. Cl.[6] ............................................. C07F 9/08
[52] U.S. Cl. ............................................. 556/480
[58] Field of Search ...................................... 332/480

[56] References Cited

U.S. PATENT DOCUMENTS

| | | | |
|---|---|---|---|
| 1,963,935 | 6/1934 | Carothers et al. | 556/480 |
| 2,628,346 | 2/1953 | MacKenzie et al. | 556/480 |
| 2,682,512 | 6/1954 | Agre | 556/480 |
| 5,358,670 | 10/1994 | Turnbull et al. | 260/665 |
| 5,629,439 | 5/1997 | Bank et al. | 556/480 |

OTHER PUBLICATIONS

Kharash et al., Grignard Reactions of Nonmetallic Substances, Prentice–Hall, Inc. NY, 1954, pp. 1306–1331.
Turk et al., Organic Synthesis, vol. 27, 7–8, 1947.
Organometallic Compounds, vol. 1, pp. 76–103 (1976), Methuen and Co. Ltd., London, U.K.
Kirk and Othmer, Encyclopedia of Chemical Technology, vol. 10, 721–734 (1996).
The Interscience Encyclopedia, Inc, NY, NY.

Primary Examiner—Paul F. Shaver
Attorney, Agent, or Firm—Melvin D. Fletcher

[57] ABSTRACT

A method for preparation of alkenylsilanes comprising contacting magnesium metal with a mixture comprising diethylene glycol dibutyl ether, an alkenyl halide, and a halosilane at a temperature within a range of about 5° C. to 200° C. The method provides a high yield of alkenylsilane product that is easily recoverable and also provides for high ratios of alkenylsilane to diethylene glycol dibutyl ether.

14 Claims, No Drawings

METHOD FOR PREPARATION OF ALKENYLSILANES

BACKGROUND OF THE INVENTION

The present invention is a method for preparation of alkenylsilanes. The method comprises contacting magnesium metal with a mixture comprising diethylene glycol dibutyl ether, alkenyl halide, and a halosilane at a temperature within a range of about 5° C. to 200° C. The method provides a high yield of alkenylsilane product that is easily recoverable and also provides for high ratios of alkenylsilane production to diethylene glycol dibutyl ether present in the method.

The reaction of organic halides with magnesium metal in the presence of solvents such as dialkyl ethers to form reactive complexes typically referred to as Grignard reagents is well known. The production and reactions of Grignard reagents has been the subject of books and numerous review articles. Such reviews are provided, for example, in Coates et al., ORGANOMETALLIC COMPOUNDS, Vol. 1, p. 76–103 (1967), Methuen and Co. LTD, London, U.K.; and in Kirk and Othmer, ENCYCLOPEDIA OF CHEMICAL TECHNOLOGY, Vol. 10, 721–734 (1966), The Interscience Encyclopedia, Inc., New York, N.Y. The Grignard reagent structure has not been determined with certainty, however it is generally believed that the Grignard reagent exists as a complex in solution and solvent can play a critical role in the complex formation. The unpredictable effect of solvent on the formation and reactivity of Grignard reagents is discussed in the above cited review articles.

The reaction of Grignard reagents with halosilanes is also well known and numerous reactions are described in Kharash et al., Grignard Reactions of Nonmetallic Substances, Prentice-Hall, Inc. NY, 1954, P. 1306–1331.

The preparation of 1,5-hexadiene, by a process using an allyl chloride Grignard reagent as an intermediate is known. For example, Turk et al., Organic Synthesis, Vol. 27, 7–8, 1947, teach a process for preparing 1,5-hexadiene by the reaction of allyl chloride in anhydrous ether with magnesium turnings. Turk et al., teach that this reaction results in the formation of a thick slurry which becomes unstirrable. This unstirrable slurry is then treated with a hydrochloric acid solution until the magnesium chloride by-product is in solution and the slurry becomes sufficiently fluid to be stirred.

The process as taught by Turk et al., is not generally acceptable as a commercial process. The formation of the non-stirrable slurry during the reaction can cause reduced mass transfer and heat transfer, resulting in reduced product. Furthermore, the nature of the slurry makes it necessary to treat the slurry in an additional step with a reagent to solubilize the slurry to allow isolation of the product. Typically, a major portion of the product is trapped within the non-stirrable slurry. Additionally, the non-flowable slurry does not allow the reaction to be run as a continuous process.

Turnbull et al., U.S. Pat. No. 5,358,670, report the formation of alkyl Grignard reagents in diethylene glycol dibutyl ether (DEGDBE). Turnbull et al., reported that Grignard reagents prepared in the presence of DEGDBE have improved yield and stability.

It is an objective of the present invention to provide a method for preparing alkenylsilanes using a Grignard-type reagent as an intermediate, where the method avoids many of the above discussed problems with Grignard type processes by creating a reaction mixture that is flowable and easily stirred. Thus, mass transfer and heat transfer can be improved in the reaction mixture providing for improved yield of alkenylsilane. In addition, the method provides for a two-phase system that allows one-step preparation of the alkenylsilane wherein the alkenylsilane can be easily separated. Furthermore, the present method reduces the amount of diethylene glycol dibutyl ether in the reaction and provides for an improved ratio of the desired alkenylsilane to by-product, when compared to known Grignard-type processes for preparing organo-substituted silanes.

SUMMARY OF INVENTION

The present invention is a method for preparation of alkenylsilanes. The method comprises contacting magnesium metal with a mixture comprising diethylene glycol dibutyl ether, alkenyl halide, and a halosilane at a temperature within a range of about 5° C. to 200° C. The method provides a high yield of alkenylsilane and decreases the mole ratio of diethylene glycol dibutyl ether to alkenyl halide used in the reaction.

DESCRIPTION OF INVENTION

The present invention is a method for preparation of alkenylsilanes. The method comprises contacting magnesium metal with a mixture comprising an alkenyl halide described by formula $$R^1X,$$ 

and about 0.01 to six moles of diethylene glycol dibutyl ether per mole of the alkenyl halide, and about 0.1 to 10 moles of a halosilane per mole of the alkenyl halide, where the halosilane is described by formula $$R^2_aH_bSiX_{4-a-b},$$ 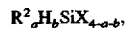

where $R^1$ is an alkenyl group comprising about two to 20 carbon atoms, each $R^2$ is an independently selected monovalent hydrocarbon comprising one to about 12 carbon atoms, X is a halogen selected from the group consisting of chlorine and bromine, $a=0$ to 3, $b=0$ to 3, and $a+b=0$ to 3, at a temperature within a range of about 5° C. to 200° C.

In the present method, by the term "one-step" it is meant that it is not necessary to isolate an intermediate Grignard type reagent in the method and further react this Grignard type reagent with the halosilane to form the alkenylsilane. Furthermore, it is not necessary to conduct a separate solubilization step on the resulting product mixture to facilitate recovery of the alkenylsilane.

The method comprises reacting magnesium metal with an alkenyl halide in the presence of a halosilane and diethylene glycol dibutyl ether (DEGDBE). The method of preparing the magnesium metal and the physical form of the magnesium metal can be any of those known in the art. The magnesium metal can be, for example, in powder, chips, or turnings form. The preferred form of magnesium metal is turnings.

Contact of the magnesium metal with the mixture comprising the alkenyl halide and the halosilane can be effected in standard reactors suitable for running Grignard type reactions. The reactor can be of a batch-type, semi-batch type, or continuous-type. A preferred reactor is a semi-batch type reactor. The environment in which the present method is run should be inert. Therefore, in a preferred method the reactor is purged and blanketed with an inert gas such as, for example, nitrogen or argon.

The mole ratio of magnesium metal to alkenyl halide fed to the reactor is not critical and can be varied within wide limits. In a batch process it is preferred that the mole ratio of magnesium metal to alkenyl halide provide alkenyl halide in sufficient excess to ensure essentially total conversion of the magnesium metal to alkenyl magnesium halide complexes. When the present method is conducted as a semi-batch process the magnesium metal is typically present in excess in relation to the alkenyl halide fed to the reactor. In such a case, the feed rate of alkenyl halide and halosilane to the reactor can be controlled to assure acceptable conversion levels of the alkenyl halide to the alkenylsilane and minimal unreacted alkenyl magnesium halide complexes. The halosilane feed may be split, with a portion being added after the magnesium bed to insure complete reaction of the alkenyl magnesium halide complex. It may also be desirable to split the solvent feed, with a portion being added after the magnesium bed to ensure complete reaction of the alkenyl magnesium halide complex. Excess alkenyl halide and halosilane added to the reactor can be recovered and recycled to the process.

Alkenyl halides useful in the present method are described by formula $R^1X$, where $R^1$ is an alkenyl group comprising about two to 20 carbon atoms and X is a halogen selected from a group consisting of bromine and chlorine. $R^1$ can be, for example, alkenyl groups such as vinyl, allyl, pentenyl, hexenyl, heptenyl, and octenyl; an cycloalkenyl groups such as cyclobutenyl, cyclopentenyl, cyclohexenyl, cycloheptenyl and, cyclooctenyl. Examples of alkenyl halides include vinylbromide, vinylchloride, allylbromide, allylchloride, and chloroprene. Preferred is when $R_1$ is an allyl group. The preferred alkenyl halides are allylchloride and allylbromide. The most preferred alkenyl halide is allylchloride.

Halosilanes useful in the present method are described by formula $R^2_aH_bSiX_{4-a-b}$, where each $R_2$ is an independently selected monovalent hydrocarbon comprising one to about 12 carbon atoms, X is a halogen selected from the group consisting of chlorine and bromine, a=0 to 3, b=0 to 3, and a+b=0 to 3. Preferred is when X is chlorine. $R^2$ for example, an alkyl such as methyl, ethyl, propyl, butyl, pentyl, hexyl, heptyl, octyl, nonyl, decyl, undecyl, and dodecyl; a cycloalkyl such as cyclopropyl, cyclobutyl, cyclopentyl, cyclohexyl, cycloheptyl, and cyclooctyl; an alkenyl such as vinyl, and allyl; a cycloalkenyl such as cyclobutenyl, cyclopentenyl, and cyclohexenyl; an aryl such as phenyl, tolyl, and naphthyl; an arylalkyl such as benzyl, beta-phenylethyl, and gamma-tolypropyl. Preferred is when $R^2$ is methyl. The preferred halosilane is selected from a group consisting of trichlorosilane, trimethylchlorosilane, dimethylchlorosilane, methyldichlorosilane, dimethyldichlorosilane, methyltrichlorosilane, tetrachlorosilane, dichlorosilane, and the bromine analogs of such chlorosilanes.

The mole ratio of alkenyl halide to halosilane can be varied within a range of about 0.1 to 10. Preferred is when the mole ratio of alkenyl halide to halosilane is within a range of about 0.8 to 3. A preferred method is where the magnesium metal is added to the process in excess to the alkenyl halide and the halosilane is added in excess to the resulting alkenyl magnesium halide intermediate. However, for safety reasons, with some halosilanes it may be desirable to run the method where the alkenyl magnesium halide intermediate is in excess.

The present method is conducted in the presence of diethylene glycol dibutyl ether (DEGDBE). About 0.01 to six moles of DEGDBE can be added to the method per mole of alkenyl halide. Preferred is when about 0.1 to one mole of DEGDBE is added to the method per mole of alkenyl halide. Even more preferred is when about 0.1 to 0.6 mole of DEGDBE is added to the method per mole of alkenyl halide.

The present method can be run at a temperature within a range of about 5° C. to 200° C. It is preferred that the present method be run at a temperature within a range of about 30° C. to 170° C. Most preferred is when the present method is ran at a temperature within a range of about 80° C. to 100° C. The pressure at which the present method is run is not critical and can be atmospheric to about 1480 kPa, however the pressure must be at or above the vapor pressure of the reaction mixture. A preferred pressure is within a range of from about atmospheric to 963 kPa.

The product of the present method is an alkenylsilane, where one or more of the halogen substituents on the silicon atom of the halosilane have been replaced by an alkenyl group. Examples of alkenylsilanes which can be prepared by the present method include, vinylchlorosilane, allylchlorosilane, butenylchlorosilane, pentenylchlorosilane, hexenylchlorosilane, cyclopentenylchlorosilane, allyltrichlorosilane, allylchlorosilane diallyldichlorosilane, diallylsilane, tetraallylsilane, allyltrimethylsilane, allyldimethylsilane, allylmethylchlorosilane, allyldimethylchlorosilane, allylmethlydichlorosilane, and diallyldimethylsilane.

The mixture resulting from conduct of the present method on standing separates into two-phases, with one phase comprising the alkenylsilane in DEGDBE and the other phase comprising a magnesium dihalide complex solubilized in DEGDBE. The alkenylsilane can be separated from the DEGDBE by, for example, distillation. The DEGDBE may be recovered from one or both phases and recycled to the method.

The following examples are provided to illustrate the present invention. The examples are not intended to limit the scope of the present claims.

EXAMPLE 1

The reaction of magnesium metal, allyl chloride, and trimethylchlorosilane in diethylene glycol dibutyl ether (DEGDBE) was evaluated. Magnesium turnings (0.24 mol), DEGDBE (0.55 mol), trimethylchlorosilane (0.17 mol), and octane (0.023 mol) as an internal standard were loaded into a glass flask equipped with a reflux condenser, addition funnel, mechanical stirrer, heating mantle, and nitrogen inlet port. The flask was purged with nitrogen and then heated to 69° C. Allylchloride (0.19 mol) was slowly added to the mixture comprising DEGDBE (0.55 mol) and trimethylchlorosilane (0.17 mol) using the addition funnel over a 1.5 hour period. The temperature of the mixture reached 120° C. The reaction mixture was stirred an additional four hours, cooled to room temperature, and then transferred to a separatory funnel and allowed to separate into two phases. The reaction mixture top phase was analyzed by gas chromatography using a flame ionization detector (GC-FID). The GC-FID analysis indicated a 62 percent yield of allyltrimethylsilane, based upon the amount of trimethylchlorosilane fed to the process, and approximately a 10:1 mole ratio of allyltrimethylsilane to 1,5-hexadiene by-product.

EXAMPLE 2

The reaction of magnesium metal, allyl chloride, and trimethylchlorosilane in diethylene glycol dibutyl ether (DEGDBE) was evaluated. Magnesium turnings (2.10 mol), DEGDBE (0.71 mol), and trimethylchlorosilane (1.96 mol) were loaded into a glass flask equipped with a reflux condenser, addition funnel, mechanical stirrer, heating mantle, and nitrogen inlet port. The flask was purged with nitrogen and then heated to 60° C. A mixture of allyl chloride (0.19 mol) and DEGDBE (2.41 mol) were slowly added to the mixture comprising the DEGDBE, and trimethylchlorosilane using the addition funnel over a 1.5 hour period. The mixture was stirred for five hours at a temperature of about 70° C. to 85° C. and cooled for 16 hours to room temperature. The mixture was then transferred to a separatory funnel to separate into two phases. The top phase containing the allyltrimethylsilane was analyzed by gas chromatography using GC-FID. The GC-FID analysis indicated a 82 percent yield of allyltrimethylsilane, based upon the amount of trimethylchlorosilane fed to the process, and approximately a 20:1 mole ratio of allyltrimethylsilane to 1,5-hexadiene by-product.

We claim:

1. A method for preparation of alkenylsilanes, the method comprising contacting magnesium metal with a mixture comprising an alkenyl halide described by formula $$R^1X,$$

about 0.01 to six moles of diethylene glycol dibutyl ether per mole of the alkenyl halide, and about 0.1 to 10 moles of a halosilane per mole of the alkenyl halide, where the halosilane is described by formula $$R^2{}_aH_bSiX_{4-a-b},$$

where $R^1$ is an alkenyl group comprising about two to 20 carbon atoms and each $R^2$ is an independently selected monovalent hydrocarbon comprising one to about 12 carbon atoms, X is a halogen selected from the group consisting of chlorine and bromine, a=0 to 3, b=0 to 3, and a+b=0 to 3, at a temperature within a range of about 5° C. to 200° C.

2. A method according to claim 1, comprising about 0.3 mole of diethylene glycol dibutyl ether per mole of alkenyl halide.

3. A method according to claim 1, comprising about 0.1 mole of diethylene glycol dibutyl ether per 0.6 mole of alkenyl halide.

4. A method according to claim 1, where the method is conducted as a semi-batch process.

5. A method according to claim 1, where the method is conducted as a batch-type process.

6. A method according to claim 1, where the method is conducted as a continuous-type process.

7. A method according to claim 1, where the temperature is within a range of about 30° C. to 170° C.

8. A method according to claim 1, where the temperature is within a range of about 80° C. to 100° C.

9. A method according to claim 1, where the halosilane is trimethylchlorosilane.

10. A method according to claim 1, where the alkenyl halide is an allyl halide.

11. A method according to claim 1 where the alkenyl halide is selected from the group consisting of allylchloride and allylbromide.

12. A method according to claim 1 where the alkenyl halide is allylchloride.

13. A method for preparation of alkenylsilanes, the method comprising contacting magnesium metal with a mixture comprising an alkenyl halide described by formula $$R^1X,$$

0.1 to less than one mole of diethylene glycol dibutyl ether per mole of the alkenyl halide, and about 0.1 to 10 moles of a halosilane per mole of the alkenyl halide, where the halosilane described by formula $$R^2{}_aH_bSiX_{4-a-b},$$

where $R^1$ is an alkenyl group comprising about two to 20 carbon atoms and each $R^1$ is an independently selected monovalent hydrocarbon comprising one to about 12 carbon atoms, X is a halogen selected from the group consisting of chlorine and bromine, a=0 to 3, b=0 to 3, and a+b=0 to 3, at a temperature within a range of about 5° C. to 200° C.

14. A method for preparation of alkenylsilanes, the method comprising contacting magnesium metal with a mixture comprising an alkenyl halide described by formula $$R^1X,$$

about 0.1 to six moles of diethylene glycol dibutyl ether per mole of the alkenyl halide, and about 0.1 to 10 moles of a halosilane per mole of the alkenyl halide, where the halosilane described by formula $$R^2{}_aH_bSiX_{4-a-b},$$

where $R^1$ is an alkenyl group comprising about two to 20 carbon atoms and each $R^2$ is an independently selected monovalent hydrocarbon comprising one to about 12 carbon atoms, X is a halogen selected from the group consisting of chlorine and bromine, a=0 to 3, b=0 to 3, and a+b=0 to 3, at a temperature within a range of about 5° C. to 200° C.

* * * * *